United States Patent [19]

Walker

[11] Patent Number: 4,471,646
[45] Date of Patent: Sep. 18, 1984

[54] BLOOD PRESSURE CUFF CALIBRATION SYSTEM

[75] Inventor: Elijah C. Walker, Takoma Park, Md.

[73] Assignee: The United States of America as represented by the Department of Health and Human Services, Washington, D.C.

[21] Appl. No.: 414,904

[22] Filed: Sep. 3, 1982

[51] Int. Cl.³ .................... G01L 27/00; A61B 5/02
[52] U.S. Cl. ............................. 73/4 R; 128/686
[58] Field of Search ............. 128/672, 677, 680, 686, 128/327, 681–683; 73/4 R

[56] References Cited

U.S. PATENT DOCUMENTS

| | | | |
|---|---|---|---|
| 3,045,470 | 7/1962 | Crandell et al. | 73/4 R |
| 3,107,515 | 10/1963 | Antonazzi et al. | 73/4 R |
| 3,459,032 | 8/1969 | Yamaguchi et al. | 73/4 R |
| 3,527,204 | 9/1970 | Lem et al. | 128/636 X |
| 3,715,925 | 2/1973 | Miller | 73/4 R X |
| 3,765,405 | 10/1973 | Natkanski | 128/686 |
| 3,812,844 | 5/1974 | Sokol | 128/686 |
| 3,868,844 | 3/1975 | Klein | 73/4 R |

FOREIGN PATENT DOCUMENTS 0928179 5/1982 U.S.S.R. .................... 73/4 R

Primary Examiner—Lee S. Cohen
Assistant Examiner—Angela D. Sykes
Attorney, Agent, or Firm—Browdy and Neimark

[57] ABSTRACT

An apparatus for measuring the pressure-transmitting characteristics of a blood pressure cuff in terms of delivered cuff pressure. It consists of a somewhat flexible cylindrical supporting tube containing a non-compressible liquid, connected to a pressure transducer. The cuff is wrapped around the tube, and the remaining exposed area of the tube is covered by a rigid cylindrical tube to prevent bulging of the supporting tube when cuff pressure is applied thereto. The cuff is pressurized while simultaneously recording its pressure and the transducer detected pressure. The resulting X-Y curve is compared with one taken of the supporting tube alone.

10 Claims, 7 Drawing Figures

BLOOD PRESSURE CUFF CALIBRATION SYSTEM

FIELD OF THE INVENTION

This invention relates to blood pressure cuffs, and more particularly to a system for measuring the pressure-transmitting characteristics of cuffs employed for the measurement of arterial blood pressure.

BACKGROUND OF THE INVENTION

In blood pressure measuring systems as now employed there is a great need to ensure that all the components of the system are operating properly. In particular, in systems of the type using an inflatable cuff it is necessary to determine, independently of use on a patient, how well any individual cuff operates, and if there are any defects, such as leakage, clogging, excessive stiffness, or the like. Thus far, no satisfactory apparatus is available for determining how much pressure from the cuff is being delivered to the surface of an appendage such as a human arm or an animal limb. Once the pressure transmission characteristics of a cuff are known, then its calibration curve can be used to provide a better determination of blood pressure.

SUMMARY OF THE INVENTION

Accordingly, an object of the invention is to overcome the deficiencies and disadvantages of the prior art, such as indicated above.

Another object is to provide for measuring the pressure-transmitting characteristics of a blood pressure cuff.

A further object of the invention is to provide an improved apparatus for measuring the pressure transmitted across the walls of a blood pressure cuff for the purpose of improving the accuracy of measurement of arterial blood pressure.

A still further object of the invention is to provide an improved system for determining how much pressure from a cuff is being delivered to the surface of an appendage such as a human arm or an animal limb, so as to obtain a calibration curve showing the pressure-transmitting characteristics of the cuff, which can be used to provide a more accurate determination of blood pressure than has heretofore been obtainable.

A still further object of the invention is to provide an apparatus for enabling a comparison to be made between a pressure transmission curve made with a particular cuff and a pressure transmission curve made with the apparatus without the cuff, such comparison indicating the ability of the cuff to transmit its internal pressure across its walls, and thus to determine its ability to deliver its pressure to the surface of an appendage such as an arm.

A still further object of the invention is to provide a cuff testing apparatus which allows one to separate the equipment concerns of blood pressure measurement from the physiological concerns, and allows a manufacturer or a standards laboratory to check the cuff properties at the time of manufacture and during its life.

A still further object of the invention is to provide a cuff testing apparatus which is easily adaptable for different sizes and widths of commercially available cuffs, or which alternatively can be made for testing specific sizes or widths of cuffs.

BRIEF DESCRIPTION OF THE DRAWINGS

Further objects and advantages of the invention will become apparent from the following description and claims, and from the accompanying drawings, wherein:

DETAILED DESCRIPTION OF A PREFERRED EMBODIMENT

Figure 1:
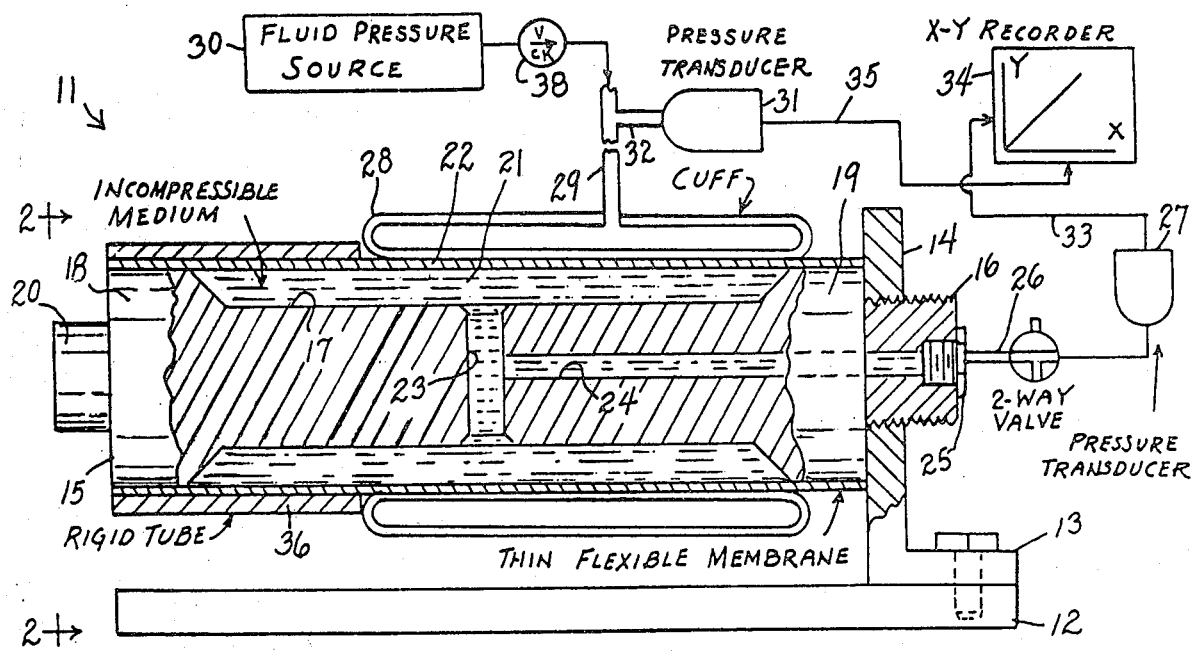
FIG. 1 is a longitudinal vertical cross-sectional view taken through a blood pressure cuff testing apparatus according to the present invention, shown with a typical cuff mounted for testing.
Figure 2:
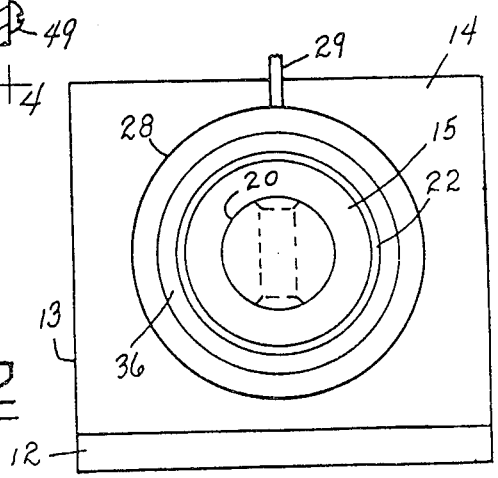
FIG. 2 is an end elevational view taken substantially on line 2—2 of FIG. 1.

Referring to the drawings, and more particularly to FIGS. 1 and 2, 11 generally designates a cuff-testing support forming part of a cuff calibrating system according to the present invention. The testing support 11 comprises an elongated base plate 12. Secured on one end of base plate 12 is an angle bracket 13 provided with the upstanding vertical arm 14. An elongated supporting block 15 has an axial threaded stud 16 which is threadedly engaged through arm 14 and is thus horizontally supported above and parallel to base plate 12. The elongated block 15 is circular in cross-section and is annularly recessed for the major portion of its length, as shown at 17, to define enlarged opposite end head members 18 and 19. The outer head member 18 is formed with an axial boss 20. Tightly and sealingly secured on the head members 18 and 19 and extending for the full length of the block 15 is a thin flexible membrane sleeve 22, of thin plastic material, or the like, which sealingly encloses the space in the elongated annular recess 17. Said space is filled with an incompressible medium 21, such as oil, water, or other liquid suitable for transmitting pressure applied to the outer surface of flexible sleeve 22.

The intermediate portion of block 15 is formed with a diametrical bore 23 communicating with an axial bore 24 extending through the rightward portion of the block, as viewed in FIG. 1, and through stud 16, being connected by a conventional fitting 25, a tubular conduit 26, and a 2-way valve to a conventional pressure transducer 27.

A blood pressure cuff 28, which is to be tested for its pressure-transmitting characteristics, is placed on the sleeve 22 adjacent to the head portion 19, as shown, and is connected via its air input conduit 29 and a check valve 38 to a suitable fluid pressure source 30, such as an air pump, or the like. A second conventional pressure transducer 31 is connected to the air supply conduit via a suitable connection tube 32.

The electrical output terminal line conductors of the first pressure transducer 27 are connected via a cable 33 to the Y-input terminals of a conventional X-Y recorder 34. The electrical output terminals of the second pressure transducer 31 are connected to the X-input terminals of recorder 34 via a cable 35.

Snugly engaged on and thus frictionally secured to the portion of the sleeve 22 not covered by the wrapped cuff 28 is a rigid restraining tube 36 which is of sufficient length to substantially cover the portion of sleeve 22 between the leftward peripheral rim of cuff 28, as viewed in FIG. 1, and the leftward end of head member 18, whereby to prevent bulging under pressure of the portion of sleeve 22 not engaged by the cuff 28.

When fluid pressure from the source 30 is applied to the wrapped cuff 28, the transducer 31 furnishes an electrical signal corresponding to such pressure via cable 35 to the X terminals of recorder 34. The resultant cuff pressure is transmitted via the sleeve 22, the incompressible liquid 21, passages 23 and 24, fitting 25 and conduit 26 to the pressure transducer 27, which thereby furnishes a Y-signal to the Y terminals of recorder 34. As the pressure in the cuff 28 builds up, a corresponding trace is recorded by the recorder 34, showing the pressure transmitted to the transducer 27 as a function of the pressure applied to the transducer 31.

Figure 3:
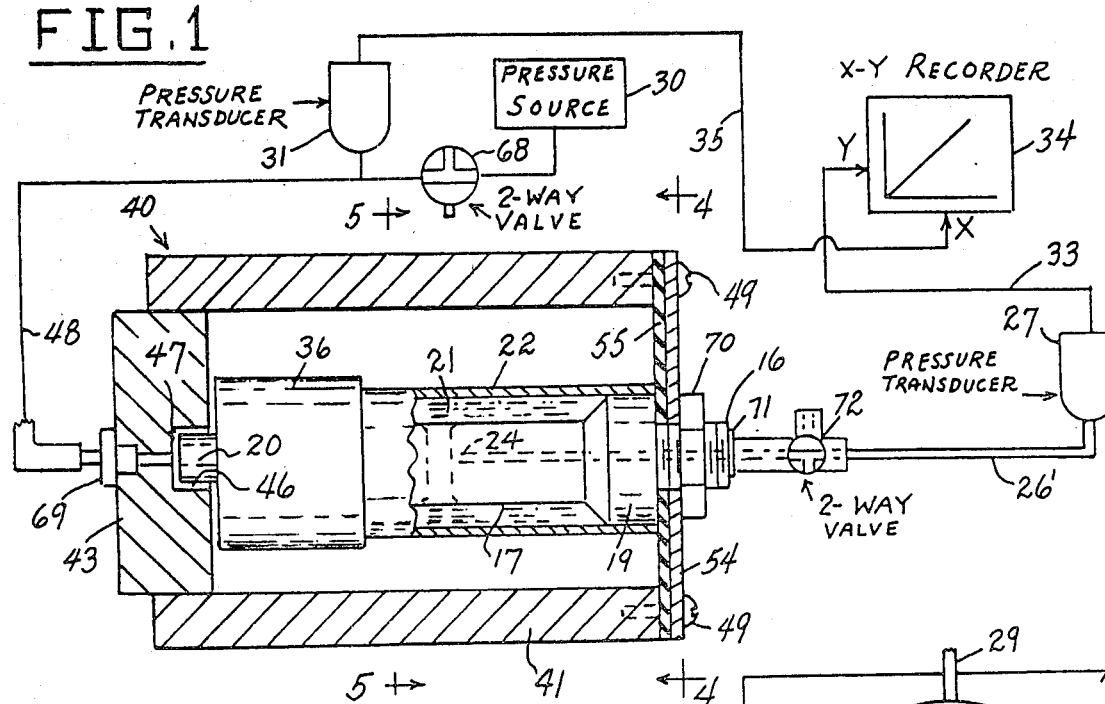
FIG. 3 is a horizontal cross-sectional view taken through a pressure chamber containing the cuff supporting member of FIG. 1, for determining the pressure-response characteristic curve of the supporting member without a cuff, to be employed for comparison with the pressure transmission curve obtained by the apparatus of FIG. 1.
Figure 4:
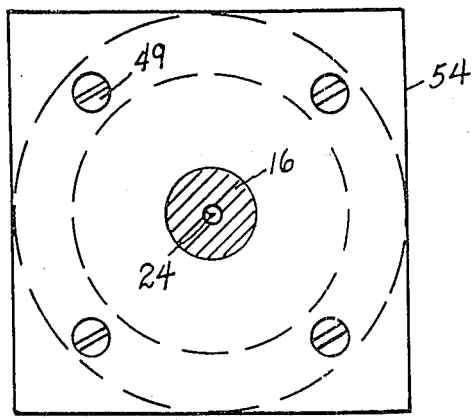
FIG. 4 is a transverse vertical cross-sectional view taken substantially on line 4—4 of FIG. 3.
Figure 5:
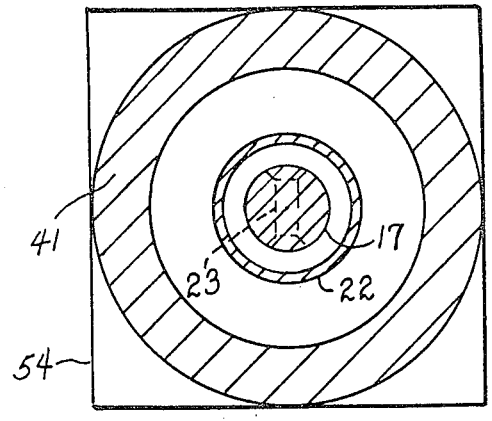
FIG. 5 is a transverse vertical cross-sectional view taken substantially on line 5—5 of FIG. 3.

The cuff pressure transmission curve thus obtained is compared with a pressure response curve obtained by testing the sensing assembly without a cuff. FIGS. 3, 4 and 5 show a pressure chamber 40 which may be employed for this purpose. Chamber 40 comprises a substantially cylindrical Plexiglas housing having a cylindrical longitudinal main wall 41 with a rigidly-secured rear end wall 43 and a square front end cover plate 54 secured to the front rim of cylindrical shell 41 by corner screws 49. A rubber sealing gasket 55 is interposed between plate 54 and the rim of cylindrical wall 41. End wall 43 is formed with a central cylindrical recess 46 which loosely receives the left end boss 20 and provides fluid clearance between said boss and the recess, as shown at 47. The fluid pressure source 30 is connected to clearance space 47 via a 2-way valve 68, a conduit 48 and a conventional connection fitting 69. Stud 16 extends through central apertures in gasket 55 and cover plate 54 and is rigidly secured to cover plate 54 by a clamping nut 70. The bore 24 is connected to the input port of the pressure transducer 27 via a conventional connection fitting 71, a 2-way valve 72 and a conduit 26'. Conduit 48 is connected to the input of pressure transducer 31. The output of said transducer 31 supplies the X-signal to the X-Y recorder 34.

The assembly of FIG. 1 is taken apart by disconnecting conduit 26 by unscrewing the fitting 25 from stud 16. A suitable plug may be employed to temporarily seal the outlet end of bore 24. The assembly comprising block 15 and the parts mounted thereon, including the liquid 21, is then unscrewed from vertical arm 14, transferred to housing 40 and inserted therein after first removing cover plate 54 and rubber gasket 55, this being done by unscrewing the fastening screws 49. Boss 20 is engaged in recess 46 and stud 16 is engaged through the registering central apertures provided in cover plate 54 and gasket 55, after which the clamping nut 70 is engaged on stud 16 and tightened. Thereafter the cover plate 54 and gasket 55 are rigidly secured to the cylindrical shell 41 by the fastening screws 49 so as to sealingly clamp the gasket 55 against the rim of shell 41. The temporary plug may then be removed from stud 16 and the input of the pressure transducer 27 may then be connected to stud 16 via conduit 26' and 2-valve 72, in place of the original conduit 26.

Figure 6:
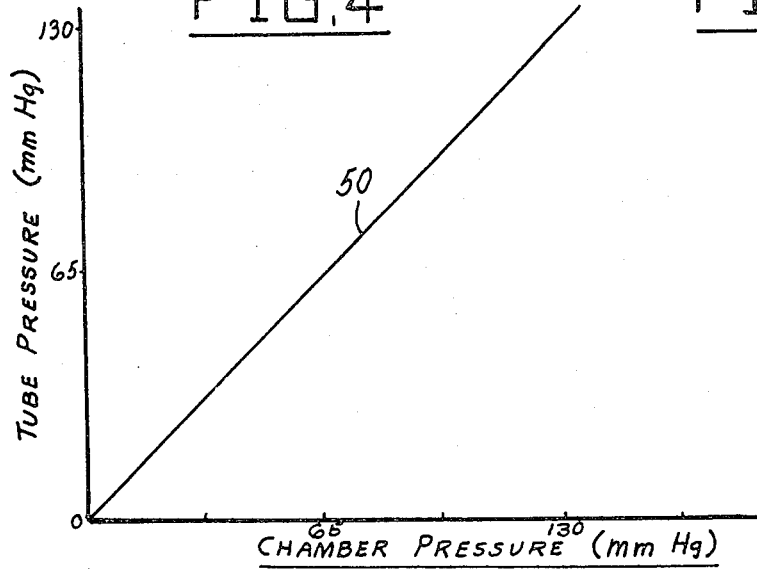
FIG. 6 is a typical pressure response curve for the cuff supporting member alone, obtained from the chamber of FIG. 3.

When fluid pressure from source 30 is applied to the housing 40, the transducer 31 furnishes an electrical signal corresponding to such pressure via cable 35 to the X terminals of recorder 34. The resultant internal pressure developed in sleeve 22 is transmitted via the incompressible liquid 21, passage 24, and conduit 26' to the pressure transducer 27, which thereby furnishes a Y-signal to the Y terminals of recorder 34. As the pressure on the liquid 21 builds up, a corresponding trace 50 (FIG. 6) is recorded by the recorder 34, showing the pressure transmitted by the sleeve 22 as a function of the pressure applied to the transducer 31.

Figure 7:
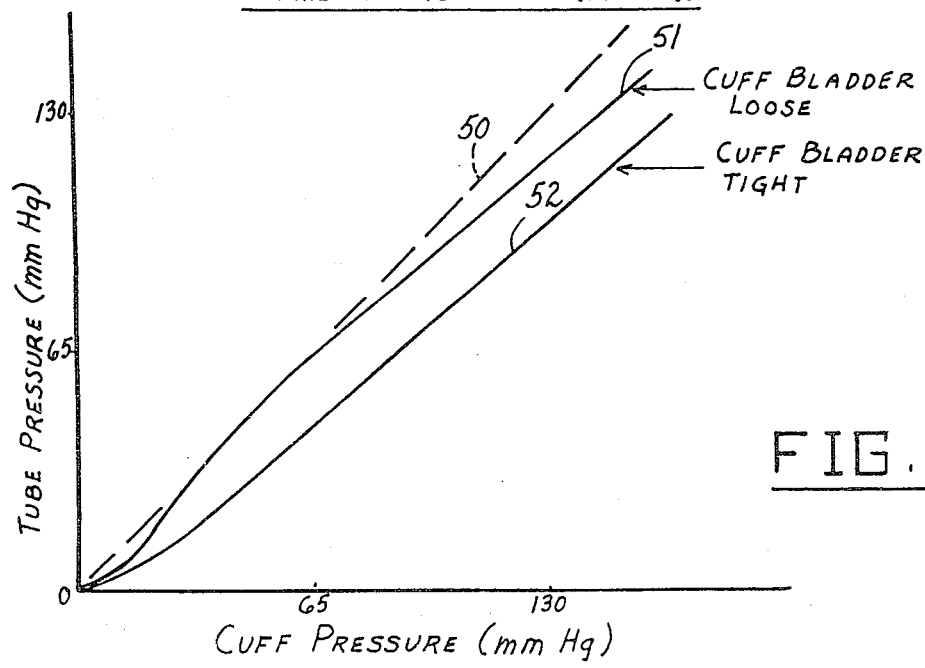
FIG. 7 is a set of pressure-transmission curves obtained from the apparatus of FIG. 1.

FIG. 7 shows typical cuff pressure transmission curves 51, 52 obtained with a typical cuff 28, employing the apparatus of FIG. 1. Curve 51 is obtained with the cuff loosely wrapped around the sleeve 22, arranged as in FIG. 1. Curve 52 is obtained with the cuff tightly wrapped around sleeve 22. In each case the curves are characteristic of the particular cuff 28 under test, and are comparable with the curve 50 obtained with the apparatus of FIG. 3 for evaluation of the performance of the particular cuff under the known test conditions, as to the pressure-transmitting characteristics of the cuff. Such evaluation is useful in determining how well the individual cuff will operate and as to the freedom of the cuff from defects such as leakage, clogging, excessive stiffness, or the like, and for determining how much pressure from the cuff will be delivered to the surface of an appendage, such as a human arm or an animal limb.

It will be noted that the calibration system above described is not the equivalent of a simulated arm because it does not consider the mechanical properties of tissue. Its sole purpose is to determine the ability of a cuff to deliver its pressure to the surface of an appendage such as an arm. It allows the user to separate the equipment aspects of blood pressure measurement from the physiological aspects. It thus provides the cuff manufacturer, or cuff standards laboratory, with the capability of determining the cuff characteristics at the time of manufacture and for monitoring said characteristics during the working life of the cuff.

When proportioning the system for use with human cuffs, a design consideration is the width of the system. If so desired, an individual system can be made for each cuff width commercially available. By providing a separate calibration system for each cuff width, the rigid anti-bulge tube 36 need not be used, enabling such artifacts as are produced by its presence to be also eliminated. However, a system capable of testing a range of cuff widths by employing appropriate-length anti-bulge tubes 36 has advantages with respect to economy.

While a specific embodiment of apparatus for measuring the pressure-transmitting characteristics of blood pressure cuffs has been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiment.

What is claimed is:

1. An apparatus for measuring the pressure-transmitting characteristics of a blood pressure cuff comprising a flexible hollow support for a wrapped cuff, substantially non-compressible fluid filling said support, means for applying a known value of fluid pressure to a cuff wrapped on said support, and means for measuring the resultant pressure transmitted by the cuff to the non-compressible fluid.

2. The measuring apparatus of claim 1, and wherein said means for measuring the transmitted pressure comprises a pressure transducer communicatively connected to the non-compressible fluid.

3. The measuring apparatus of claim 1, and substantially rigid anti-bulge means covering a portion of the support not covered by the wrapped cuff.

4. The measuring apparatus of claim 3, and wherein said anti-bulge means comprises a substantially rigid tube closely surrounding the portion of the support not covered by the wrapped cuff.

5. The measuring apparatus of claim 1, and means for plotting the measured pressure transmitted by the cuff to the non-compressible fluid against the pressure applied to the cuff, for deriving a pressure calibration curve characteristic of the cuff for a plurality of applied pressures.

6. The measuring apparatus of claim 1, and means to derive a pressure response characteristic of the support alone for comparison with the measured pressure transmitted by the cuff to the non-compressible fluid.

7. The measuring apparatus of claim 6, and wherein the means to derive said pressure characteristic of the support alone comprises a sealed chamber, means to mount the support in said chamber, means to apply a known value of fluid pressure to the interior of said chamber, and means for measuring the resultant pressure transmitted through the support to said non-compressible fluid.

8. The measuring apparatus of claim 7, and wherein the means to derive said pressure characteristic of the support comprises means to plot the pressures transmitted to said non-compressible fluid against a plurality of known values of fluid pressure applied to the interior of the chamber, whereby to derive a characteristic curve.

9. The measuring apparatus of claim 1, and wherein said means for measuring the transmitted pressure comprises a first pressure transducer communicatively connected to the non-compressible fluid, and a second pressure transducer communicatively connected to the means for applying fluid pressure to the cuff for measuring the applied pressure.

10. The measuring apparatus of claim 9, and an X-Y recorder, and means connecting the outputs of the first and second pressure transducers respectively to the Y and X inputs of said X-Y recorder.

* * * * *